United States Patent [19]

Van Lindert

[11] Patent Number: 5,346,484
[45] Date of Patent: Sep. 13, 1994

[54] CUSHION-LIKE MEMBER FOR ABDOMINAL OPERATIONS

[76] Inventor: Arnold C. M. Van Lindert, Lorentzlaan 179, NL-3707 HH Zeist, Netherlands

[21] Appl. No.: 958,254

[22] Filed: Oct. 8, 1992

[30] Foreign Application Priority Data

Oct. 8, 1991 [NL] Netherlands .................. 9101692

[51] Int. Cl.$^5$ ............... A61F 13/15; A61F 13/20; A61F 13/00
[52] U.S. Cl. ................... 604/358; 604/369; 128/846; 128/849; 128/850; 602/46
[58] Field of Search ............ 128/846, 849, 850, 851, 128/853; 604/304, 308, 358, 346, 369; 602/903, 46, 60–61, 6 C

[56] References Cited

U.S. PATENT DOCUMENTS

| 1,944,009 | 1/1934 | Homer . | |
|---|---|---|---|
| 2,630,119 | 3/1953 | Aagesen | 604/379 |
| 3,288,131 | 11/1966 | Garland . | |
| 4,848,364 | 7/1989 | Bosman | 128/850 |
| 4,889,107 | 12/1989 | Kaufman . | |

FOREIGN PATENT DOCUMENTS

| 3122954 | 1/1983 | Fed. Rep. of Germany . | |
|---|---|---|---|
| WO8001239 | 6/1980 | PCT Int'l Appl. . | |
| 9104680 | 4/1991 | World Int. Prop. O. | 604/389 |

Primary Examiner—Randall L. Green
Assistant Examiner—P. Zuttarelli
Attorney, Agent, or Firm—Webb Zeisenheim Bruening Logsdon Orkin & Hanson

[57] ABSTRACT

In abdominal operations, particularly gyneacological abdominal operations, gauze-like material is often used in practice to hold organs such as intestines away from the operative area. This gauze-like material must in many cases be replaced during an operation and also lacks the desired stiffness to hold the intestines in particular in place in all cases.

The present invention provides a cushion-like member for inserting into a relatively large body cavity, as formed during abdominal/pelvis surgery, and for restraining one or more body organs (for instance the intestines) and/or for absorbing blood and/or wound fluid, wherein the cushion-like member consists substantially of synthetic, absorbent material and has a outer contour of such shape that it is layable along and or beyond an edge of said body cavity.

14 Claims, 1 Drawing Sheet

CUSHION-LIKE MEMBER FOR ABDOMINAL OPERATIONS

BACKGROUND OF THE INVENTION

In abdominal operations, particularly gyneacological abdominal operations, gauze-like material is often used in practice to hold organs such as intestines away from the operative area. This gauze-like material must in many cases be replaced during an operation and also lacks the desired stiffness to hold the intestines in particular in place in all cases.

Experiments have taken place on a limited scale with restraining members for intestines in particular operations. These have been found inadequate in practice, for instance because of the inadequate shape, stiffness and-/or flexibility.

The retro-peritoneal vessels extend along the spinal column and have a thickness of about 2 cm. Pressure on the retro-peritoneal vessels may lead to brain damage due to lack of an adequate supply of blood. Care must be taken to avoid pressure on the retro-peritoneal vessels during surgery.

SUMMARY OF THE INVENTION

The present invention provides a cushion-like member for inserting into a relatively large body cavity, as formed during abdominal/pelvis surgery, and for restraining one or more body organs (for instance the intestines) and/or for absorbing blood and/or wound fluid, wherein the cushion-like member consists substantially of synthetic, absorbent material and has a outer contour of such shape that it is layable along and or beyond an edge of said body cavity.

The cushion-like member according to the present invention can be inserted without much effort, because of the outline or outer contour thereof.

WO 80/01239 discloses a rod shaped surgical device, which comprises a non-elastically deformable flexible member, surrounded by a soft liquid absorbing material. This rod shaped surgical device has to be adapted to the shape of the body cavity.

A preferred embodiment of the shape of the cushion-like member is somewhat horseshoe-like, such that the cushion-like member is held in position from all sides.

Preferably the synthetic absorbent material is a P.V.A. hydro foam, which has high absorbent characteristics as well as cushion-like properties. If necessary, this material can also be cut, e.g. by a pair of scissors or a knife, to further improve the shape thereof.

BRIEF DESCRIPTION OF THE DRAWINGS

Further advantages, features and details of the present invention will be elucidated in the light of a description of a preferred embodiment thereof, with reference to the annexed drawings, in which.

DESCRIPTION OF THE PREFERRED EMBODIMENT

A cushion-like member 1 according to the present invention is provided with rounded side 2 or convex outer contour 2 and a side or concave inner contour 3 located opposite which incorporates a recess. The shown preferred embodiment has a thickness d of approximately 23 mm and a height h of approximately 120 mm, a length $l_1$ of approximately 234 mm and a breadth $l_2$ of the recess of approximately 108 mm.

The cushion-like member 1 is preferably manufactured from polyvinylalcohol (P.V.A.) which, in combination with the chosen form which has a somewhat horseshoe-like appearance, has a sufficient stiffness to hold the intestines away from the operative area during an abdominal operation. The cushion-like member 1 is slightly foldable due to both the material and the specific shape of the cushion-like member 1, so that it can easily be placed in the correct position and pressed fixedly therein. Since the material is cushion-like, contact trauma of the intestinal body organs or bowels is avoided.

The recess and overall shape and material of the cushion-like member 1 provide that pressure is not exerted on the retro-peritoneal vessels (to the rear of the peritoneum), nor is indirect pressure exerted on the midriff. The texture of the material prevents the cushion-like member sliding away. The P.V.A. is preferably used in the form of an absorbent micro-porous foam, as known in other applications, for instance for plastic splint material (as a substitute for plaster) and temporary skin-substitute material. The P.V.A. is immunologically inert.

The cushion-like member 1 is preferably moisture sterilized with gamma radiation. The cushion-like member 1 may be prepackaged in a peel pack which may be opened by pulling two lips from each other. The cushion-like member 1 may be packaged in the peel pack after being moistened, and the package, may then be sterilized by gamma radiation after sealing. The packaging can be easily pulled open, whereafter the cushion-like member is immediately ready for use for an operation in the abdomen or on the pelvis.

Figure 1:
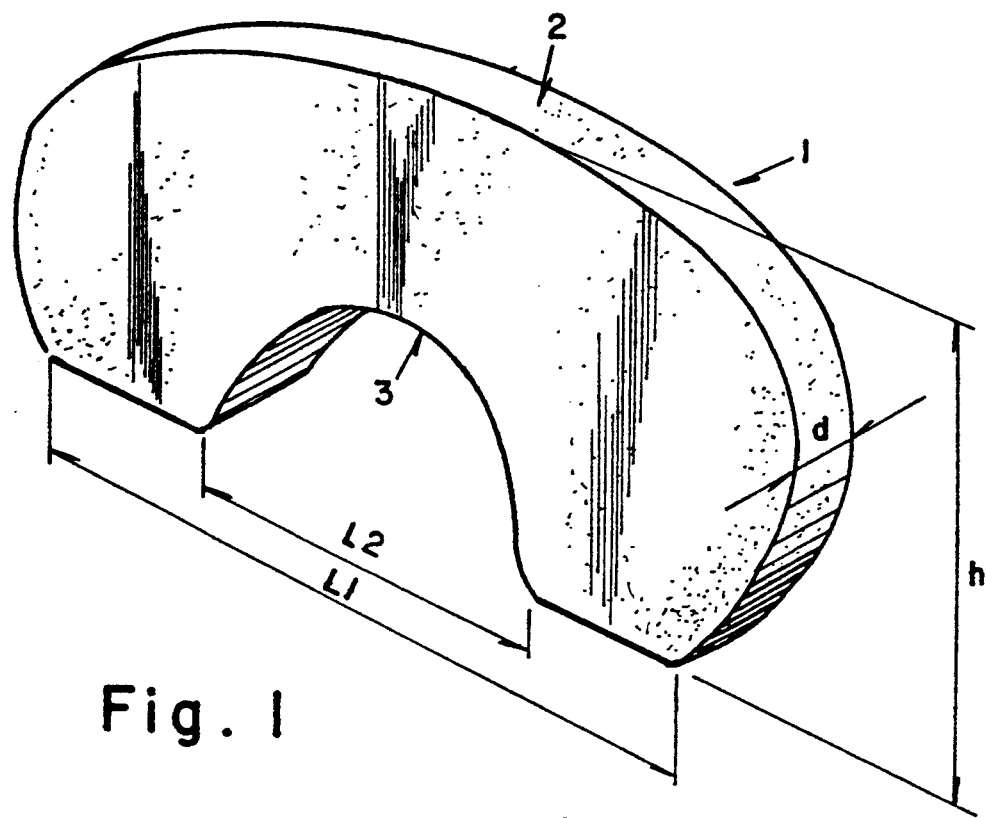
FIG. 1 shows a side view in perspective of a preferred embodiment of the cushion-like member according to the present invention.
Figure 2:
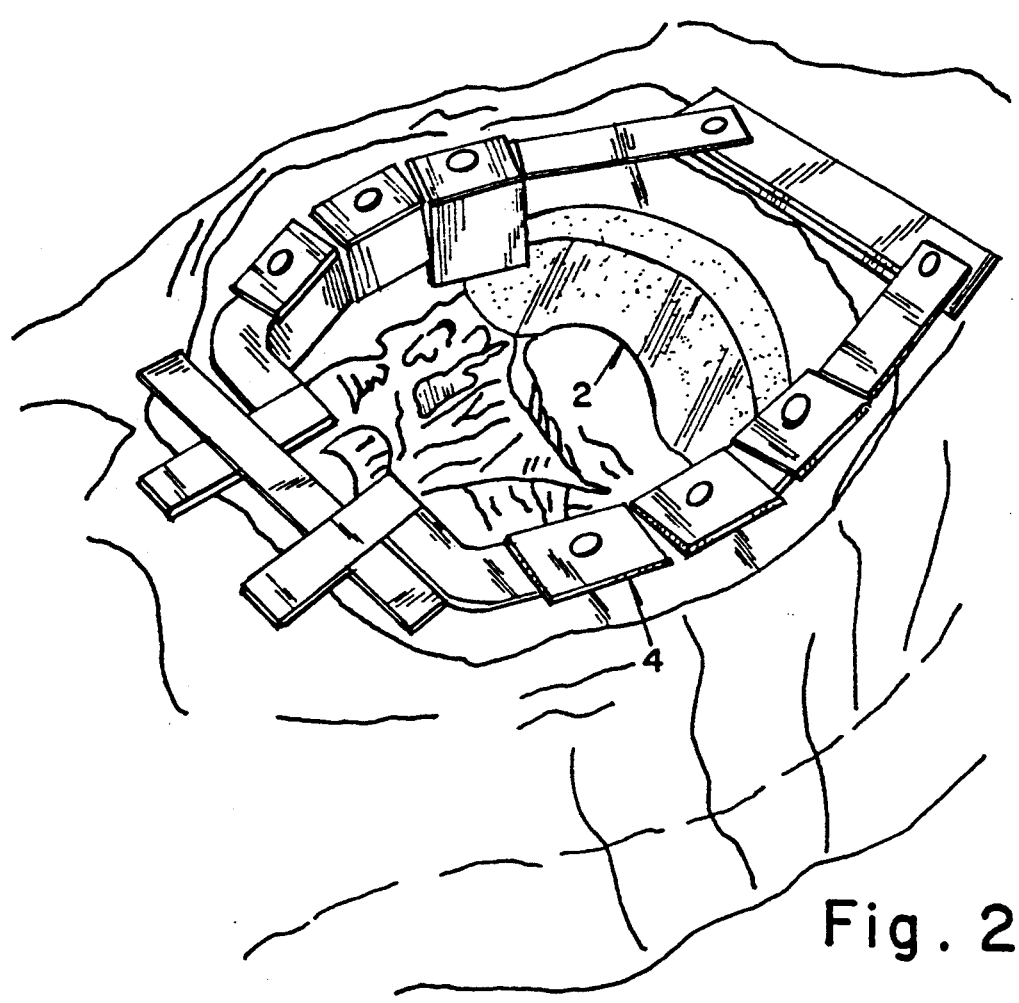
FIG. 2 is a view in perspective of the member of FIG. 1 applied during an operation.

FIG. 2 shows the cushion-like member in use during an abdominal operation, wherein use is also made of an implement 4 for holding open the surgical opening.

It should be apparent from FIG. 2 that the body organs on which an operation has to be performed are clearly visible so that the surgeon (or gynecologist) can perform his meticulous work optimally. The cushion-like member 1 holds the intestines located therebehind out of sight of the surgeon, while blood and wound fluid are absorbed and all possible conceivable complications are avoided.

I claim:

1. A flexible cushion member for insertion into a body cavity formed during surgery for restraining at least one body organ, said member formed of an absorbent material for absorbing blood and other fluids and having a preformed outer contour adapted for use in said body cavity, wherein a portion of said outer contour is convex, and a portion of said cushion member which is opposite said convex portion is concave in shape and defines a recess therein for eliminating pressure on retro-peritoneal vessels in said body cavity during use of said flexible cushion member.

2. The cushion member as claimed in claim 1, wherein said absorbent material is polyvinylalcohol hydro foam, and said cushion member is sterilized with gamma radiation.

3. The cushion member as claimed in claim 1 wherein said cushion member has a thickness of approximately 23 mm, a height of approximately 120 mm, and a length of approximately 234 mm, and wherein said recess has a breadth of approximately 108 mm.

4. The cushion member as claimed in claim 1, wherein said cushion member has a thickness, a height, a length which is approximately 95% larger than said height, and a breadth of said recess which is approximately 90% of said height.

5. The cushion member as claimed in claim 4 wherein said thickness is approximately 23 mm.

6. A flexible, sterilized intestinal retraction pad for insertion into a patient's abdominal cavity during surgical operations to hold intestines of said patient out of an operating cavity, said pad being formed of a synthetic, absorbent material for absorbing blood and other fluids, said pad having a preformed outer contour, wherein a portion of said outer contour contacts said intestines to hold said intestines out of said operating cavity and is convexly shaped; and a recess means formed in said pad for eliminating pressure on retro-peritoneal vessels of said patient during use of said intestinal retraction pad.

7. The pad of claim 6 wherein said recess means is formed on a side of said pad which is opposite to said convexly shaped portion.

8. The pad of claim 7 wherein said recess means is defined by a concavely shaped portion of said pad.

9. The pad of claim 8 wherein said pad is formed of polyvinylalcohol hydro foam.

10. The pad of claim 9 wherein said pad has a thickness, a height, a length which is approximately 95% larger than said height, and a breadth of said recess means which is approximately 90% of said height.

11. The pad of claim 9 wherein said pad has a thickness of approximately 23 mm, a height of approximately 120 mm, a length of approximately 23 mm, and a breadth of said recess means of approximately 108 mm.

12. A method of intestinal retraction during surgical procedures comprising the insertion of a flexible, sterilized retraction pad into a patient's abdominal cavity during surgical operations to hold intestines of said patient out of an operating cavity, said pad being formed of a synthetic, absorbent material for absorbing blood and other fluids, said pad having an outer contour, wherein a portion of said outer contour contacts said intestines to hold said intestines out of said operating cavity and is convexly shaped; and a recess means formed in said pad for eliminating pressure on retro-peritoneal vessels of said patient during use of said intestinal retraction pad wherein said convexly shaped portion is positioned facing away from said operation cavity and said recess means is positioned such that no pressure is exerted on said retro-peritoneal vessels.

13. The method of claim 12 further comprising the preliminary steps of packaging the pad prior to use and moistening said pad prior to packaging; said package comprising a peel package; and sterilizing said package and pad by gamma radiation after said package has been sealed.

14. The method of claim 12 wherein said pad is slightly folded during insertion for proper positioning.

* * * * *